United States Patent [19]

Fujisaki

[11] Patent Number: 4,933,960
[45] Date of Patent: Jun. 12, 1990

[54] FILTER SELECTION METHOD FOR HARD X-RAY ANALYSIS OF OBJECTS

[76] Inventor: Yukio Fujisaki, 705, Daiichi-Kodan, 20-23, Hakataeki-mae 4-chome, Hakata-ku, Fukuoka-shi, Fukuoka 812, Japan

[21] Appl. No.: 299,538

[22] Filed: Jan. 23, 1989

[30] Foreign Application Priority Data

Jan. 28, 1988 [JP] Japan .................................. 63-18687

[51] Int. Cl.$^5$ .......................................... G01N 23/06
[52] U.S. Cl. ..................................... 378/53; 378/157; 378/207
[58] Field of Search ......................... 378/53, 157, 207

[56] References Cited
U.S. PATENT DOCUMENTS 3,854,049  12/1974  Mistretta ............................ 378/157
4,727,561  2/1988   Fujisaki ............................... 378/54

Primary Examiner—Craig E. Church
Attorney, Agent, or Firm—Leydig, Voit & Mayer

[57] ABSTRACT

A measuring method employing hard X-rays receives a hard X-ray beam from an X-ray source at first and second sensors substantially simultaneously. The beam directly reaches the first sensor but reaches the second sensor only after penetrating an object to be analyzed and a filter. The ratio of intensity values of the beams detected at the sensors is calculated so that filters producing X-ray absorption coefficients substantially independent of the thickness of objects to be analyzed are identified. Zt, the sum of the products of the atomic numbers Z and thicknesses t of each of the filter members of the identified filters, fall on a straight line graph of Zt versus X-ray tube voltage. Subsequently, filters are quickly selected from the graph during an analysis of objects of similar composition with hard X-rays. Alternatively, for a particular filter the proper X-ray tube voltage may be quickly selected from the straight line graph to produce an absorption coefficient substantially independent of object thickness.

12 Claims, 4 Drawing Sheets

FILTER SELECTION METHOD FOR HARD X-RAY ANALYSIS OF OBJECTS

TECHNICAL BACKGROUND OF THE INVENTION

This invention relates to measuring methods employing hard X-rays and, more specifically, to such a method that make quantitative measurements with high detection accuracy utilizing hard X-rays, i,e., having wavelengths below 1 Å, without damaging an object being measured.

The hard X-ray measuring method of the type referred to is effectively employed in such various fields as the medical field for diagnoses of internal organs, bones and teeth, in the industrial field for discrimination of various substances and materials and their deterioration, quality and like inspections. This is because the method allows the X-ray wavelength to be optionally selectable by varying voltage applied to the X-ray source. Hard X-rays have extremely short wavelengths and are relatively safe for the human body while having very high penetrability. Thus, the object to be measured can be any substance in any phase such as gas, liquid, sol, gel, powder, or solid.

DISCLOSURE OF PRIOR ART

In the field of measurement and inspection by means of X-rays, quantitative measurements have been long believed impossible with the use of the hard X-rays i.e., X-rays having wavelengths below 1 Å, even though their penetrability is increased. Therefore, hard X-rays below 1 Å have not been employed in quantitative measurement and inspection.

The present inventor has noticed remarkable features of hard X-rays such as excellent penetrating characteristics, less hazard to the human body, and easy shielding from the human body. A result of studies and development by the inventor has been disclosed in Japanese Published Utility Model Application 57-20648. According to that study, quantitative measurements are achieved with a double sensor mechanism comprising a pair of sensors for real time reception of hard X-rays from a single X-rays source. One of the sensors directly receives an X-ray beam from the source while the other sensor receives an X-ray beam emitted from the same source but after passage through an object to be measured.

The present inventor has further disclosed in the U.S. Pat. No. 4,727,561 a measuring arrangement in which, in addition to that of the foregoing Japanese Utility Model Publication, a table on which the object to be measured is placed is made movable. One of the other sensors comprises an image receiving camera and a spot X-ray sensor which are alternately, positionable for receiving X-rays. A filter means including a pair of filter parts corresponding to the pair of the sensors is disposed between the X-ray source and the sensors with the pair of the filter parts arranged so that the relation between the thickness of the object to be measured and the absorption coefficient of the hard X-rays can be expressed as a linear function. With this measuring arrangement, the measurement can be improved in its adaptability to the inspection of metallic fatigue, determination of deterioration or available life time, and the like.

In this United States Patent, the measuring operation is carried out by varying the voltage applied to the X-ray source tube in response to the material of the object to be measured or its thickness, and disposing one of the filter parts forming the filter between the X-ray source and the other sensor. Here, filter parts are selected empirically with respect to the object to be measured or, the filter parts are sequentially investigated until a filter part suited for the quantitative measurement is identified. Further, when the object to be measured is variable between one material such as a plastic, liquid or the like which requires only a low tube voltage and an other material as a metal, ceramic or the like which requires a high tube voltage, it is necessary to replace the filter with another having filter parts of different types. When, in addition, the object to be measured is an entirely novel one, a filter having proper filter parts must be prepared on the basis of empirical information or through repetitive tests and corrections, i.e., the filter parts must be sequentially investigated to select an optimum filter. Accordingly, there have been problems left unsolved in that the selection of the filter parts calls for a highly skilled operator of the measuring apparatus or method, the measuring has been rather time consuming, a different filter is required for each different type object being measured.

TECHNICAL FIELD OF THE INVENTION

A primary object of the present invention is, therefore, to provide a measuring method employing hard X-rays on the basis of an entirely novel hard X-ray measuring technique. In the method, measurement accuracy is remarkably improved, a proper filter for the X-ray source tube voltage is quickly selected for every different type object to be measured, and, if required, an appropriate new filter can be promptly prepared.

According to the present invention, the above object can be attained by providing a method for hard X-ray analysis of an object in which the hard X-rays not penetrating through the object received by a first sensor, hard X-rays from the same source that penetrate through a filter and the object are received by a second sensor. The intensity of the hard X-rays detected at the first sensor is used as a reference value, and the ratio of the intensity of the X-rays detected at the second sensor with respect to the reference value is obtained for inspecting the object. A filter is selected which does not vary the linear absorption coefficient with by the thickness of the object with an X-ray tube voltage that varies more than a factor of two by making the total Zt value i.e., the sum of the products of the atomic number and the thickness of each of the filter members fall approximately on a substantially straight line of Zt plotted against X-ray tube voltage.

It should be appreciated that, with the above arranged method according to the present invention, the filter can be quickly selected or, if required, the filter can be preliminarily prepared to determine an appropriate filter the work required for the X-ray measurement can be simplified to a large extent.

Other objects and advantages of the present invention should be made clear in following description of the invention detailed with reference to an embodiment shown in accompanying drawings.

Figure 1:
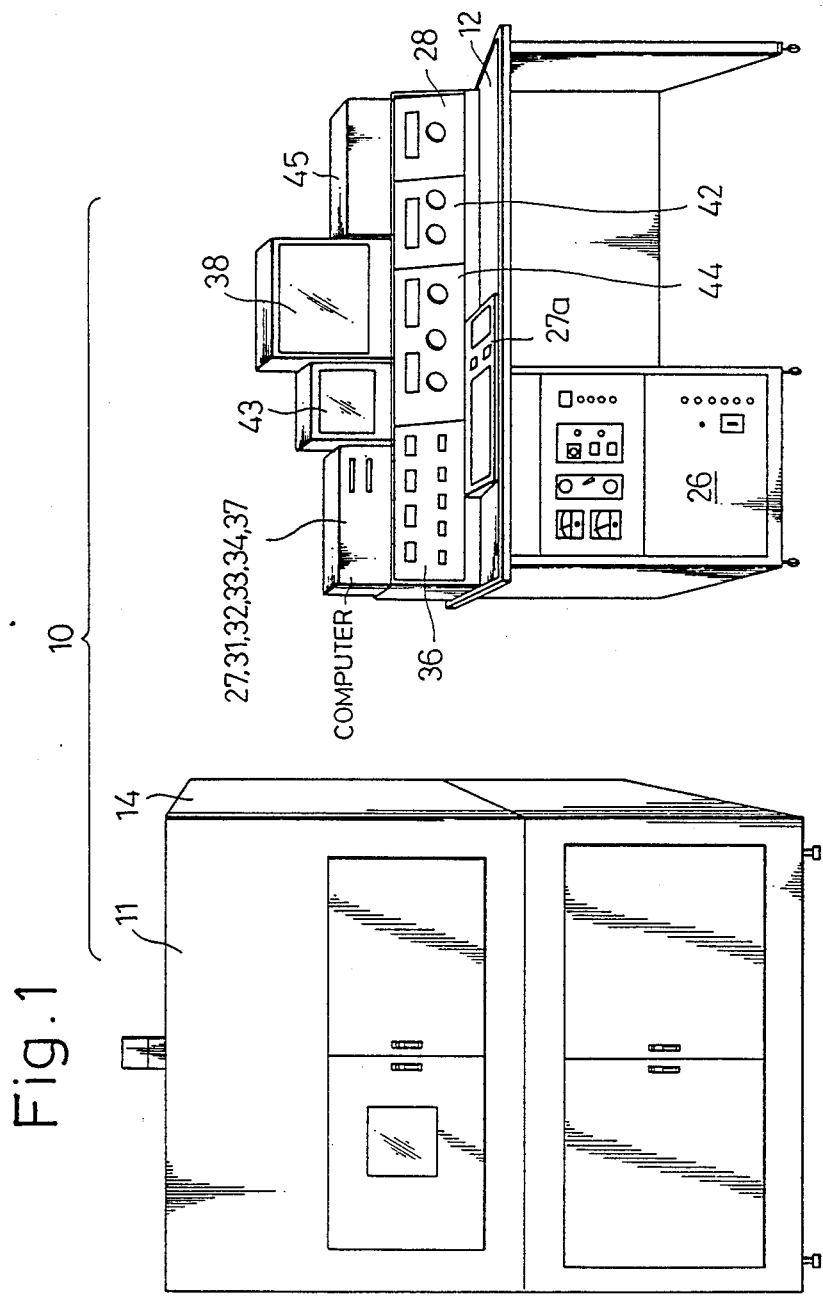
FIG. 1 is a perspective view showing an entire apparatus for carrying out the method for hard X-ray measurement according to the present invention.

While the present invention shall now be explained with reference to the embodiment shown in the drawings, it should be appreciated that the intention is not to limit the invention only to such embodiment shown but rather to include all alterations, modifications and equivalent arrangements possible within the scope of appended claims.

DISCLOSURE OF PREFERRED EMBODIMENT

Figure 2:
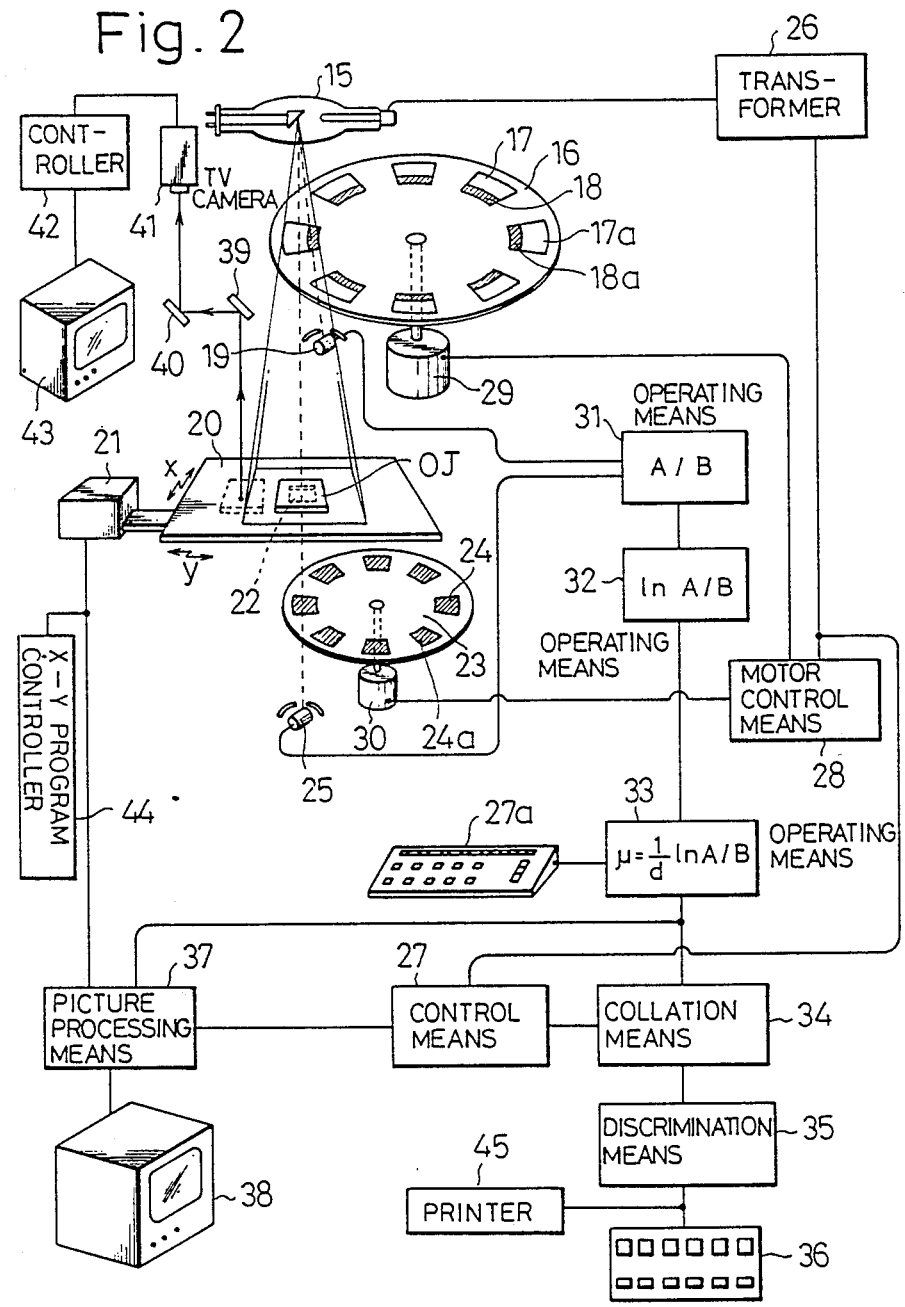
FIG. 2 is a block diagram showing schematically a part of the apparatus of FIG. 1.

Referring to FIGS. 1 and 2, there is shown an apparatus 10 employed for practicing the hard X-ray measuring method according to the present invention, which generally comprises a measuring section 11, a processing section 12 including a computer, and a display section 13. In the top part of an X-ray shielding housing 14, an X-ray source 15 is disposed for emitting hard X-rays, i.e., X-rays of wavelengths less than 1 Å, and a first rotary filter disc 16 is disposed just below the X-ray source 15. This rotary filter disc 16 is formed with irradiating windows 17, 17a, ... 17n disposed circumferentially on the disc and spaced from each other. Filters 18, 18a, ... 18n for zero-point correction are secured in these windows 17, 17a, ... 17n but are disposed only on radially inward edge side of the windows. These zero-point correcting filters 18, 18a, ... 18n are mutually different in filtering action corresponding respectively to each of a variety of the X-ray tube voltages. Further below the first rotary filter disc 16, a first X-ray sensor 19 is disposed for directly receiving a hard X-ray beam emitted from the source 15 after passage through one of the zero-point correcting filter members 18, 18a, ... 18n but before reaching an object OJ to be analyzed.

Within the housing 14 and below the X-ray source 15 and rotary filter disc 16, a table 20 for carrying thereon the object OJ is disposed. Table 20 is coupled to a driving unit 21 to be freely moveable at least in two directions, i.e., along x and y axes, or preferably in three directions i.e., along x, y and z axes. The table 20 has an aperture in the central part where the object OJ is to be placed. Further below this table 20, there is disposed a second rotary filter disc 23 having disposed along its periphery main filters 24, 24a, ... 24n which are mutually separated for filtering the hard X-ray beam that penetrates the object OJ to be analyzed and the aperture 22. Disposed still further below this second rotary filter disc 23 is a second X-ray sensor 25 for receiving the X-ray beam filtered through one of the main filters 24, 24a, ... 24n after being emitted from the source 15 and penetrating the object OJ on the table 20.

The hard X-ray source 15 is connected through a transformer 26 to a control means 27 in the processing section 12 for controlling the irradiation cycle of the source. This control means 27 also provides its control output to a motor control means 28 for controlling motors 29 and 30 respectively driving the first and second rotary filter discs 16 and 23. That is through the control means 27, the voltage applied to the X-ray tube 15 is established, the motors 29 and 30 are synchronously rotated, and one of the zero-point correcting filters 18, 18a, ... 18n as well as one of the main filters 24, 24a, ... 24n respectively corresponding to the established tube voltage are thereby disposed within the beam path from the X-ray source 15 to each of the first and second sensors 19 and 25.

An output A of the first sensor 19 and an output B of the second sensor 25 are supplied to a division means 31 to produce a ratio A/B of the sensor outputs. The ratio is supplied to a logarithm means 32 which produces a logarithmic value, $\ln A/B$ of the ratio. This logarithmic value is supplied to an operating means 33 to determine the linear absorption coefficient. Information on the thickness d of the object OJ is also provided to the operating means 33 from a keyboard 27a of the processing section 12, so that the linear X-ray absorption coefficient $\mu = 1/d \cdot \ln A/B$ is calculated in the operating means 33. This calculated value of $\mu$ is supplied to a collation means 34 in which the value $\mu$ is compared to and collated with all information on the object being analyzed that is stored in a memory means of the control means 27. The collation result is supplied to a discrimination means 35, where material, structure and so on of the object being analyzed are processed and are displayed by a display means 36 and a printer 45. The calculated value of $\mu$ is also supplied from the operating means 33 to a picture processing means 37 to which information on the position of the table 20 is also provided from the table driving unit 21. The analysis of the object OJ is displayed on a screen 38 on the basis of the linear absorption coefficient $\mu$ and positional information, in the same manner as that disclosed in the foregoing U.S. Pat. No. 4,727,561.

In the foregoing arrangement, it is desirable to place the object OJ precisely and reliably at the position where the X-rays are incident. In the present instance, an image of the object OJ on the table 20 is monitored by a TV camera 41 through mirrors 39 and 40. The monitored image is presented through a controller 42 for focusing the camera 41 on an object positioning screen 42. The object's position is adjusted by moving the table 20 in the direction of the x and y axes and, if required, also in the direction of the z axis so that an optional analysis point of the object OJ (as shown, for example, by dotted lines in addition to the object shown by solid lines for convenience of easier illustration) coincides with a reference point established on the screen 43. Then the table 20 is moved along the x and y axes while controlling the driving unit 21 preferably by means of an x-y program controller 44 to align the analysis point of the object OJ with the X-ray incident position.

Figure 4:
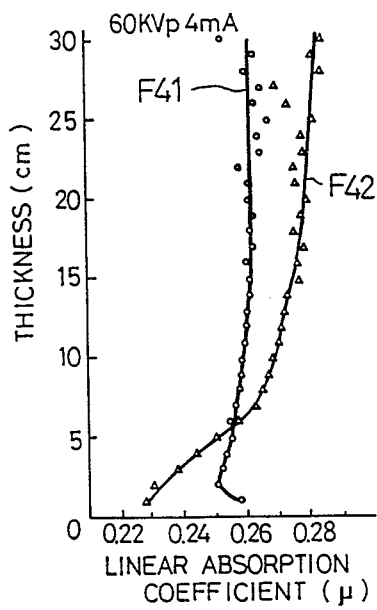
FIG. 4 is a diagram showing the relationship between object thickness and the linear absorption coefficient with a 60 KVp tube voltage.
Figure 5:
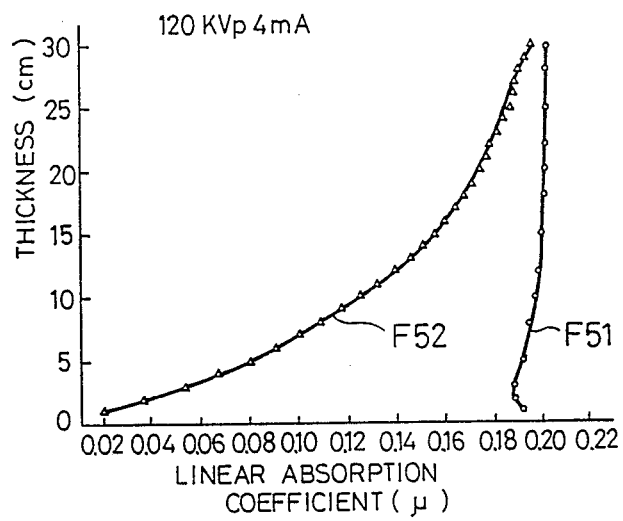
FIG. 5 is a diagram showing the relationship between object thickness and the linear absorption coefficient with a upon 120 KVp X-ray tube voltage.

According to a remarkable feature of the present invention, filters may be chosen which show no substantial change in the linear absorption coefficient $\mu$ with the thickness of the object being analyzed even when the X-ray tube voltage is varied by more than a factor of 2. A substantially constant linear absorption coefficient $\mu$ irrespective of the thickness d of the object OJ is obtained. Here, the filter was selected with an X-ray tube current of 4 mA, X-ray tube voltages of 60 KVp and 120 KVp and a variable thickness d acrylic plate. It was found that, in the case of the tube current of 4 mA and the tube voltage of 60 KVp, the use of a filter formed by a laminate, i.e., filter members of 0.2 mm thick Al and 0.3 mm thick Cu showed an excellent result. The relationship between the thickness d and the linear absorption coefficient $\mu$ in the above measurement is shown in FIG. 4 by a curve F41. By contrast, a curve F42 in FIG. 4 shows the relationship between acrylic plate thickness d and the linear absorption coefficient in an event where no filter is employed. The total Zt, i.e., the sum of the products of the respective atomic numbers Z and thicknesses t of each of the filter members is 11.3. It has been also found that, in the case of an X-ray tube current of 4 mA and an X-ray tube voltage of 120 KVp, a filter member comprising a laminate of 1.04 mm thick Cu and 0.3 mm thick Ag is excellent for quantitative analysis. In FIG. 5, the relationship of acrylic plate thickness d to the linear absorption coefficient $\mu$ is shown by a curve F51. By contrast, a curve F52 shows the relationship between the acrylic plate thickness d and the coefficient $\mu$ when no filter was employed. In this case, the total Zt, i.e., the sum of the products of the atomic numbers Z and thicknesses t of each of the filter members is 44.3.

Figure 3:
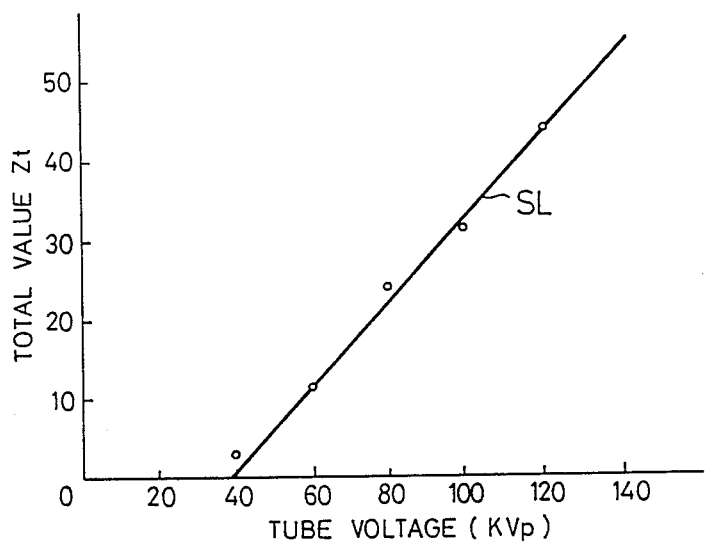
FIG. 3 is a diagram showing relationship between the X-ray tube voltage and the total Zt value i.e., the sum of the products of the atomic numbers and the thickness of each of the filter elements

Here, as shown in FIG. 3, a straight line SL is drawn on an x-y coordinate graph showing the relationship between the hard X-ray tube voltage and the total Zt values as reported above having. Next, filters Zt values which fall on the straight line SL or closely approximate the line were designed for X-ray tube voltages 40 KVp, 80 KVp, and 100 KVp. The filter member materials and thicknesses are shown in the following table:

| Tube Voltage | Zt from FIG. 3 | Filter Members and Thicknesses | Filter Zt |
| --- | --- | --- | --- |
| 40 KVp | 0.3 | Cu 0.1 mm thick | 2.9 |
| 80 KVp | 22.3 | Al 0.3 mm thick & Cu 0.7 mm thick | 24.1 |
| 100 KVp | 33.3 | Cu 0.6 mm thick & Ag 0.3 mm thick | 31.5 |

Figure 7:
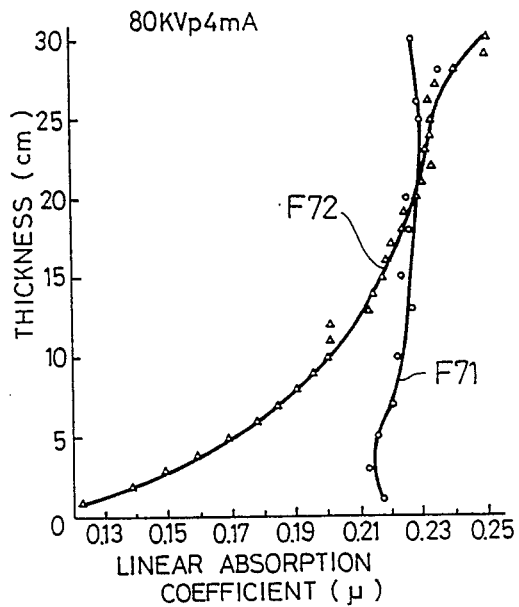
FIG. 7 is a diagram showing the relationship between object thickness and the linear absorption coefficient with a upon 80 KVp tube voltage.
Figure 6:
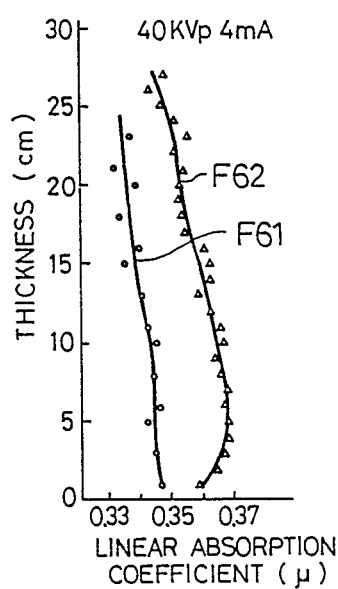
FIG. 6 is a diagram showing the relationship between object thickness and the linear absorption coefficient with a upon 40 KVp X-ray tube voltage.
Figure 8:
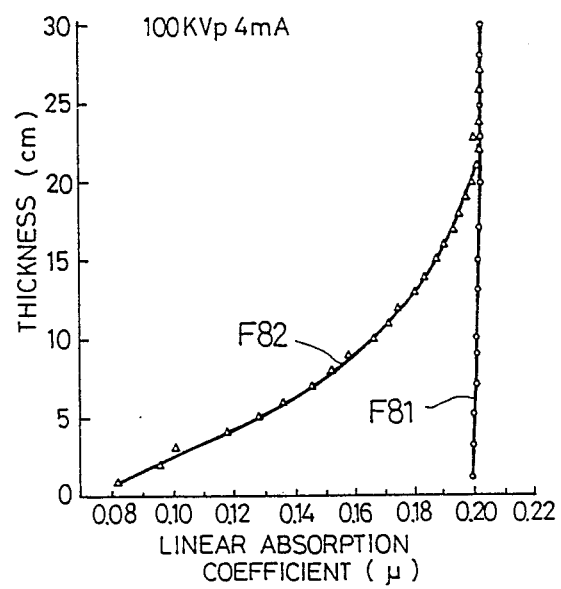
FIG. 8 is a diagram showing the relationship between object thickness and the linear absorption coefficient with a upon 100 KVp X-ray tube voltage.

The relationship between the acrylic plate thickness d and the linear absorption coefficient $\mu$ under these tube voltages was measured for these filter members, and, as proved by curves F61, F71 and F81 of FIGS. 6, 7 and 8, respectively, shown in contrast to curves F62, F72 and F82 representing similar relationship but without using the filters, these filters have been found capable of making the linear absorption coefficient $\mu$ to be substantially independent of object thickness. It has been found from the straight line SL in FIG. 3 that the filter could be sufficiently effectively employed so long as the total Zt value was within ±10% of the straight line SL.

According to the measuring method of the present invention, as will be readily appreciated, the selection of the proper filter when the tube voltage of the hard X-ray source is varied in response to the type of the object to be measured can be easily and quickly determined to simplify the measuring operation.

In the present invention, various design modifications are possible. For example, instead of the foregoing arrangement of moving the object OJ for its precise positioning, the object carrying table 20 may be fixed and the X-ray source 15, first and second sensors 19 and 25, motors 29 and 30, mirrors 39 and 40, TV camera 41, and so on may be arranged to be mutually and integrally movable with respect to the object OJ. Further, while the foregoing arrangement has been referred to as employing the rotary filter disks 16 and 23 having many filter members, rotary filter disks 16 and 23 may be replaced by a detachable filter holder to make the zero point correcting and main filters freely manually exchangeable to simplify the arrangement.

What is claimed is:

1. A measuring method employing hard X-rays comprising irradiating hard X-rays by applying a voltage to an X-ray tube, detecting the X-rays at a first sensor directly from said X-ray tube, passing the X-rays through combinations of at least two filters with a plurality of test objects of the same composition and of different thicknesses, detecting at a second sensor the X-rays that have penetrated the combinations of filters and test objects, and determining the ratios of the intensities of the X-rays detected at said second sensor to the intensity of the X-rays detected at the first sensor to determine whether the linear absorption coefficient of the X-rays is substantially independent of the thicknesses of the test objects, passing X-rays irradiated from said tube through a main filter disposed adjacent a specimen object, and selecting said filter including at least one filter member so that the total value of the products of a parameter and the thickness of each filter member will at least closely approximate a substantially straight line graph of said total value versus said tube voltage derived from the ratio measurements.

2. A method according to claim 1 including selecting said main filter so that the linear absorption coefficient is substantially constant irrespective of the thickness of said object to be measured when said hard X-ray tube voltages vary by more than a factor of two.

3. A method according to claim 1 wherein said filter selecting step is carried out by rendering said total value to approximate said straight line within ±10%.

4. A method according to claim 1 comprising placing a zero-point correcting filter between the X-ray tube and said first sensor.

5. A method according to claim 4 including disposing a plurality of main filters and zero-point correcting filters along the circumferences of respective rotatable discs and synchronously rotating said discs to place selected main filters and zero-point correcting filters between the X-ray tube and said second sensor.

6. A measuring method employing hard X-rays comprising emitting hard X-rays from an X-ray tube by applying a voltage to the X-ray tube, detecting the X-rays at a first sensor directly from the X-ray tube, passing the X-rays through combinations of each of at least two filters, each filter including at least one filter member, and a plurality of test objects of the same composition and of different thicknesses with at least two different voltages applied to the X-ray tube, detecting at a second sensor the X-rays that have penetrated the combinations of filters and the test objects, determining the ratio of the intensity of the X-rays detected at the second sensor to the intensity of the X-rays detected at the first sensor to determine whether an X-ray absorption coefficient of the test objects in combination with each of the filters is substantially independent of the respective thicknesses of the test objects for a particular voltage, plotting, for two filters producing X-ray absorption coefficients substantially independent of the thicknesses of the test objects for a particular voltage, on a graph having one axis for X-ray tube voltage and a second orthogonal axis for a filter characteristic, two X-ray tube voltages and the characteristic of the corresponding filters, the filter characteristic equaling the sum of the products of the respective atomic numbers and thicknesses of each of the filter members of the filter, drawing a straight line intersecting the points plotted on the graph, selecting from the plotted straight line one of an X-ray tube voltage and a filter characteristic and thereby a filter when the other of the X-ray tube voltage and filter characteristic are known in order to carry out hard X-ray analysis of a specimen object of the same composition as the test objects with an X-ray absorption coefficient independent of the thickness of the specimen object.

7. The method according to claim 6 wherein said filter characteristic and filter are selected from the straight line graph based upon a filter X-ray tube voltage to fall within ± ten percent of said straight line.

8. The method according to claim 6 wherein said X-ray voltage is selected from the straight line graph based upon a fixed filter characteristic to fall within ± ten percent of said straight line.

9. A method of selecting a filter for use in hard X-ray analysis of a specimen object so that an X-ray absorption coefficient substantially independent of the thickness of the specimen object is obtained comprising:

irradiating a plurality of test objects having different thicknesses and the same composition as a specimen object with hard X-rays through each of at least two filters, each filter including at least one metallic foil member, by applying a fixed voltage, that is different for each filter, to an X-ray tube;

measuring the intensity of the hard X-rays after passage through the respective filters and the test objects to determine which filters produce X-ray absorption coefficients for the test objects substantially independent of the respective thicknesses of the test objects;

establishing a straight line relationship between two points of X-ray voltage and corresponding filter characteristics that produce X-ray absorption coefficients substantially independent of the respective thickness of the test objects, the filter characteristic for each respective filter being the sum of the products of the respective atomic numbers and thicknesses of each of the foil members of each filter; and selecting a filter having a filter characteristic at least approximately meeting the straight line relationship for X-ray analysis of a specimen object at a particular X-ray tube voltage.

10. The method according to claim 9 wherein said filter is selected to meet the straight line relationship of X-ray tube voltage and filter characteristic within ± ten percent.

11. A method of selecting an X-ray tube voltage for use in hard X-ray analysis of a specimen object so that an X-ray absorption coefficient substantially independent of the thickness of the specimen object is obtained comprising:

irradiating a plurality of test objects having different thicknesses and the same composition as a specimen object with hard X-rays through each of at least two filters, each filter including at least one metallic foil member, by applying a fixed voltage, that is different for each filter, to an X-ray tube;

measuring the intensity of the hard X-rays after passage through the respective filters and the test objects to determine which filters produce X-ray absorption coefficients for the test objects substantially independent of the respective thicknesses of the test objects;

establishing a straight line relationship between two points of X-ray voltage and corresponding filter characteristics that produce X-ray absorption coefficients substantially independent of the respective thickness of the test objects, the filter characteristic for each respective filter being the sum of the products of the respective atomic numbers and thicknesses of each of the foil members of each filter; and selecting an X-ray tube voltage at least approximately meeting the straight line relationship for X-ray analysis of a specimen object with a filter having a particular filter characteristic.

12. The method according to claim 11 wherein said X-ray tube voltage is selected to meet the straight line relationship of X-ray tube voltage and filter characteristic within ± ten percent.

* * * * *